(12) United States Patent
Wiedemann et al.

(10) Patent No.: US 7,600,542 B2
(45) Date of Patent: Oct. 13, 2009

(54) BEVERAGE BOTTLING PLANT FOR FILLING BOTTLES WITH A LIQUID BEVERAGE FILLING MATERIAL HAVING A TREATMENT SECTION

(75) Inventors: Ulrich Wiedemann, Dortmund (DE); Jan Münzer, Dortmund (DE)

(73) Assignee: KHS Maschinen- und Anlagenbau AG, Dortmund (DE)

( * ) Notice: Subject to any disclaimer, the term of this patent is extended or adjusted under 35 U.S.C. 154(b) by 590 days.

(21) Appl. No.: 10/984,677

(22) Filed: Nov. 9, 2004

(65) Prior Publication Data

US 2005/0126656 A1   Jun. 16, 2005

(30) Foreign Application Priority Data

Nov. 10, 2003   (DE)   ................. 103 52 886

(51) Int. Cl.
*B65B 1/04*   (2006.01)
(52) U.S. Cl. .............. 141/91; 141/85; 141/89; 53/127; 53/425
(58) Field of Classification Search ............. 141/85–89, 141/91, 92; 99/453, 456, 457, 467, 470; 53/127, 425
See application file for complete search history.

(56) References Cited

U.S. PATENT DOCUMENTS

| | | | | |
|---|---|---|---|---|
| 4,441,406 A | * | 4/1984 | Becker et al. ................. 99/275 |
| 4,490,401 A | * | 12/1984 | Becker et al. ............... 426/407 |
| 5,012,727 A | * | 5/1991 | Pesente ........................ 99/470 |
| 5,566,695 A | * | 10/1996 | Levey et al. .................. 134/83 |
| 5,750,174 A | * | 5/1998 | Lucassen .................... 426/521 |
| 5,772,958 A | | 6/1998 | Nielsen |
| 6,142,065 A | * | 11/2000 | Panella et al. ................ 99/468 |
| 6,189,440 B1 | * | 2/2001 | Amundson ................... 99/455 |
| 6,374,575 B1 | | 4/2002 | Dittrich et al. |
| 6,588,327 B2 | * | 7/2003 | Wakabayashi et al. ........ 99/470 |
| 6,834,473 B2 | * | 12/2004 | Wiedemann ................. 53/127 |
| 2002/0073652 A1 | | 6/2002 | Wiedemann |
| 2002/0170440 A1 | | 11/2002 | Wakabayashi et al. |

FOREIGN PATENT DOCUMENTS

| | | |
|---|---|---|
| DE | 12 17 762 B | 5/1966 |
| DE | 17 92 383 B | 11/1971 |
| DE | 230 695 A | 12/1985 |
| DE | 297 16 644 U1 | 1/1998 |
| DE | 203 17 441 U | 6/2004 |
| ES | 2 184 533 A1 | 4/2003 |
| WO | WO 95/22352 | 8/1995 |

OTHER PUBLICATIONS

European Patent Office Search Report EP 04 02 5622 and English translation thereof.

* cited by examiner

*Primary Examiner*—Timothy L Maust
(74) *Attorney, Agent, or Firm*—Nils H. Ljungman & Associates

(57) ABSTRACT

A pasteurization station for pasteurizing a product in containers having a tunnel housing that is formed in a modular configuration from any desired number of flexible, exchangeable segments, each of which is interchangeable with at least one other of said segments and comprises a portion of the housing, a container conveyor, and liquid dispensers.

8 Claims, 7 Drawing Sheets

BEVERAGE BOTTLING PLANT FOR FILLING BOTTLES WITH A LIQUID BEVERAGE FILLING MATERIAL HAVING A TREATMENT SECTION

BACKGROUND

1. Technical Field

The present application relates to a beverage bottling plant for filling bottles with a liquid beverage filling material, having a treatment section for the treatment of products in containers as described herein below.

2. Background Information

A beverage bottling plant for filling bottles with a liquid beverage filling material can possibly comprise a beverage filling machine with a plurality of beverage filling positions, each beverage filling position having a beverage filling device for filling bottles with liquid beverage filling material. The filling devices may have an apparatus designed to introduce a predetermined volume of liquid beverage filling material into the interior of bottles to a substantially predetermined level of liquid beverage filling material. The apparatus designed to introduce a predetermined flow of liquid beverage filling material further comprises an apparatus that is designed to terminate the filling of the beverage bottles upon the liquid beverage filling material reaching the predetermined level in bottles. There may also be provided a conveyer arrangement that is designed to move bottles, for example, from an inspecting machine to the filling machine. Upon filling, a closing station closes the filled bottles. There may further be provided a conveyer arrangement configured to transfer filled bottles from the filling machine to the closing station. Bottles may be labeled in a labeling station, the labeling station having a conveyer arrangement to receive bottles and to output bottles. The closing station and the labeling station may be connected by a corresponding conveyer arrangement.

In the beverage industry, especially when bottling highly perishable products, it is customary to treat them. In treatment plants of the prior art, the containers with the products are conveyed in a practically uniform and continuous movement from the entry area to the exit area. During this movement, they are heated until they have absorbed the desired number of treatment units, then cooled, whereupon the treatment process is ended. A treatment tunnel provided for the purpose consequently has a heating section, a superheating and treatment section and a subsequent cooling section. The individual sections can have additional sub-zones. The gradual heating and cooling thereby achieved is preferred in particular for the glass bottles used in the beverage industry, to avoid the destruction of the glass bottles by abrupt temperature changes. The transfer of heat to the product contained in the bottles is normally achieved by spraying said containers with water as they are moved along on a conveyor belt which allows the sprayed liquid to pass through from below. Underneath the conveyor belt are catch basins for the sprayed fluid, from which the pumps used for the spraying are fed. Between the heating and cooling sections, heat can be exchanged with the sprayed liquid in the individual zones.

To achieve an optimum graduation of the temperatures in the individual sections, the sections are appropriately subdivided. Generally, the "heating" section has three to four individual zones, the treatment section has two or three zones, and an additional superheating zone can also be provided upstream of the treatment zone. The subsequent "cooling" section in turn has three to four individual zones in which the containers are cooled to the desired exit temperature by decreasing the temperature of the sprayed liquid in steps.

The spray temperatures that are set at any given time are adjusted so that they are appropriate to the product, the length of the zones and the speed of the conveyor belt to ensure that the product in the bottles achieves the specified degree of treatment.

Consequently, during production operation, the minimum amount of heat that must be supplied to the treatment tunnel is the amount that is necessary to heat the beverage and the containers from their temperature on entry to the temperature on exit, with an intermediate heating to the treatment temperature followed by a cooling.

For the spraying of the containers, in the treatment housing, oriented at right angles to the direction of transport, there are a plurality of spray tubes with spray nozzles or spray openings next to one another and at a distance from one another, and a lateral fluid feed. Spray tubes of this type are known from DE 297 166 44, for example.

OBJECT OR OBJECTS

On the basis of a treatment plant of the type described above, the object is to reduce the time, effort and expense required for the manufacture, assembly and start-up of these plants and their treatment housings, and to create standardized housing modules, preferably for almost all types of realizations.

SUMMARY

The present application teaches that the treatment housing is formed in a modular configuration from any desired number of flexible, exchangeable interchangeable segments, whereby these segments are oriented at a right angle to or parallel to the direction of conveyance of the treatment device, and can be positioned and lined up next to one another on zone tanks or hot water tanks that are oriented parallel to or along this conveyor device.

With this configuration and the features disclosed in the other claims, as well as in this description, the result is simple housing base modules that have a high percentage of identical parts and that permit series production of many components. In addition, there is a more flexible zone structure for an optimal machine design, whereby the essentially standardized housing modules are suitable for almost all types of realizations of heat treatment machines for containers such as treatment devices, coolers, heaters etc.

In one possible embodiment, the bottling temperature of the beverage before it is dispensed into the beverage bottles is elevated by the heat of the treatment plant, and the filled beverage bottles are conducted to the treatment plant at this elevated product temperature, whereby the recycled cooled process fluid is used at least in one zone of the cooling section.

In another possible embodiment, the beverage is preheated with a process medium of the treatment, the temperature of which is only slightly above the bottling temperature.

Consequently, with these process sequences in combination, a recuperative heat exchange, which is itself part of the prior art, in combination with the pre-heating of the beverage as taught by the present application before the filling process achieves a cooling of the beverage containers in the final section of the treatment tunnel, to a lower exit temperature. The result is a significant reduction in the total amount of heat required for the treatment tunnel. It must thereby be taken into account that the amount of heat that is present in the beverage containers as they exit the treatment tunnel, can be recycled into the heating of the beverage as recovered heat, if a spray medium is available to apply a significant temperature gradient toward the exit temperature to the beverage bottles. The present application thereby teaches that the use of a heat exchanger in the cold beverage stream upstream of the filling machine ensures a significantly more effective transfer of heat. The cooling temperature for the exit side of the treatment tunnel is thereby only a few degrees higher than the storage and/or bottling temperature of the beverage.

The embodiments are explained in greater detail below on the basis of one exemplary embodiment, whereby reference is made to a treatment plant of the prior art of the type described in DE 199 08 035 A1, for example.

The above-discussed embodiments of the present invention will be described further hereinbelow. When the word "invention" or "embodiment of the invention" is used in this specification, the word "invention" or "embodiment of the invention" includes "inventions" or "embodiments of the invention", that is the plural of "invention" or "embodiment of the invention". By stating "invention" or "embodiment of the invention", the Applicant does not in any way admit that the present application does not include more than one patentably and non-obviously distinct invention, and maintains that this application may include more than one patentably and non-obviously distinct invention. The Applicant hereby asserts that the disclosure of this application may include more than one invention, and, in the event that there is more than one invention, that these inventions may be patentable and non-obvious one with respect to the other.

BRIEF DESCRIPTION OF THE DRAWINGS

The embodiments are explained in greater detail below on the basis of one exemplary embodiment which is illustrated in the accompanying FIGS. 1 to 5.

DESCRIPTION OF EMBODIMENT OR EMBODIMENTS

Figure 1A:
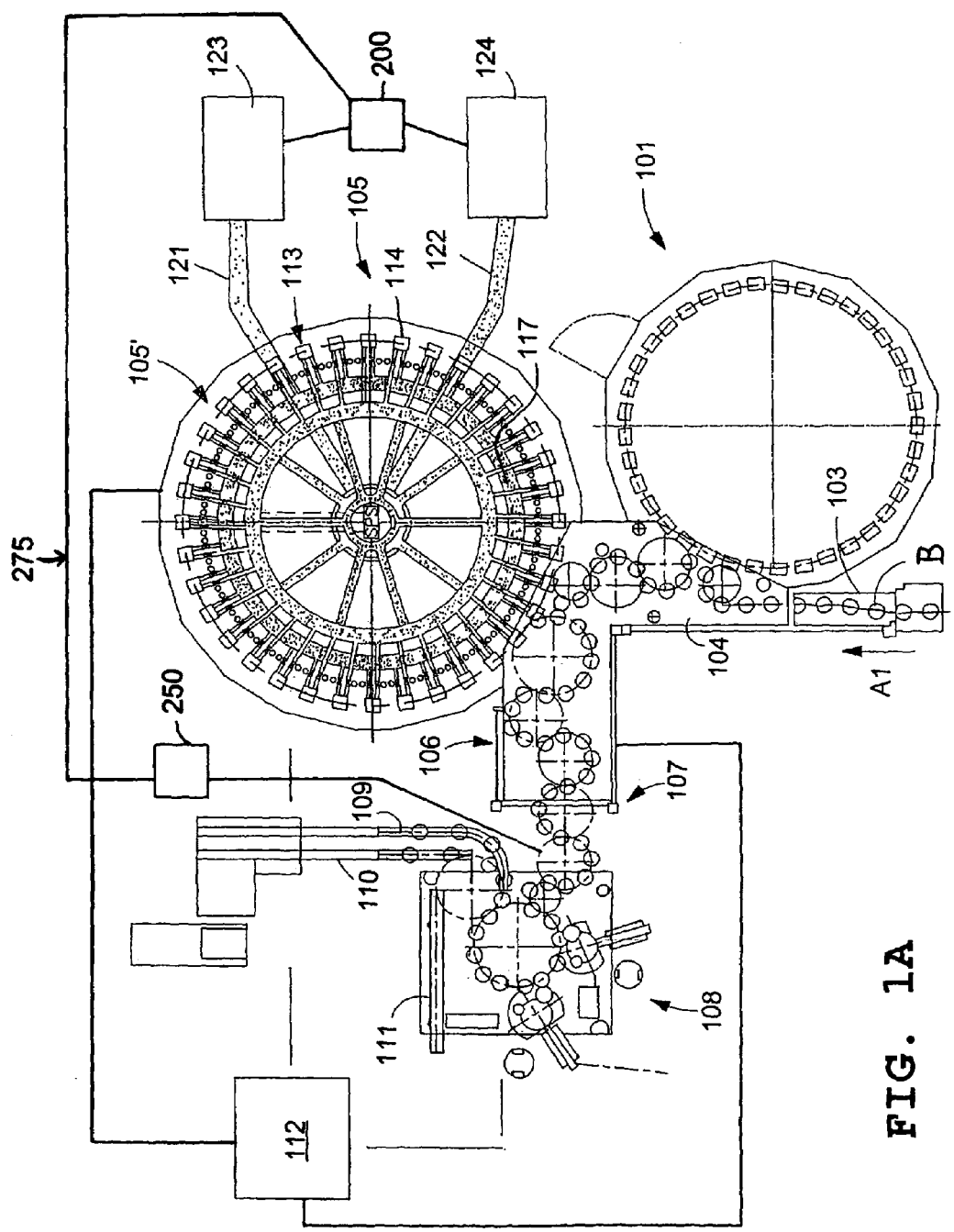
FIG. 1A is a schematic illustration of a container filling plant in accordance with one possible embodiment.

Further development details, advantages and possibilities of application of the application can be obtained from the following description of embodiments and the drawing. With this, all described and/or illustrated features per se or in any combination, comprise the substance of the application, regardless of their combination in the claims or their dependency. At the same time, the content of the claims is made a component of the description.

FIG. 1A shows schematically the main components of one embodiment example of a system for filling containers, specifically, an embodiment of a beverage bottling plant 100 for filling bottles B with liquid beverage filling material, in accordance with one embodiment, or in which system or plant could possibly be utilized at least one aspect, or several an aspects, of the embodiments disclosed herein.

FIG. 1A shows a rinsing arrangement or rinsing station 101, to which the containers, namely bottles B, are fed in the direction of travel as is indicated by the arrow A1, by means of a conveyer line or conveyer arrangement to feed bottles to rinsing arrangement 103, and downstream of rinsing arrangement or rinsing station 101, in the direction of travel as is indicated by the arrow A1, the rinsed bottles B are transported to a beverage filling machine 105 by means of a conveyer line or conveyer arrangement 104 to pass bottles to filling machine that is formed, for example, by a starwheel conveyer or a plurality of starwheels of a conveyer arrangement. The conveyer arrangement 104 to pass bottles to filling machine may possibly comprise a starwheel conveying structure that introduces bottles B to the filling machine 105.

Downstream of the filling machine 105, in the direction of travel of the bottles B, there can preferably be a closing arrangement or closing station 106 which closes the bottles B.

The closing arrangement or closing station 106 can, for example, be connected directly to a labeling arrangement or labeling station 108 having at least one labeling unit, device, or module for first product, each unit having a head, such as, for example, by means of a conveyer arrangement 107 to pass bottles to labeling arrangement that may be formed, for example, by a plurality of starwheels of a conveyer arrangement.

In the illustrated embodiment, the labeling arrangement or labeling station 108 having at least one labeling unit, device, or module for first product, each unit having a head has, for example, three outputs, namely one output formed by a conveyer arrangement 109 to convey first product bottles for bottles B that are filled with a first product. The first product may possibly be provided by a first product mixer 123 that is connected to the filling machine 105, for example, through a conduit for first product 121, and bottles B that are filled with a predetermined volume of liquid beverage filling material, that is, the first product, are then labeled by a labeling module in the labeling arrangement or labeling station 108 having at least one labeling unit, device, or module for first product, each unit having a head, corresponding to this first product delivered from first product mixer 123 to the beverage filling machine 105 and thence to the corresponding bottles B.

A second output that is formed by a conveyer arrangement 110 to convey second product bottles is provided for those bottles B that are filled with a second product. The second product may emanate from a second product mixer 124 that is connected, for example, through a conduit for second product 122 to the filling machine 105, and these bottles B filled with a predetermined volume of liquid beverage filling material comprising the second product are then correspondingly labeled by a labeling module in the labeling arrangement or labeling station 108 having at least one labeling unit, device, or module for first product, each unit having a head, corresponding to this second product.

A third output, for example, formed by a conveyer arrangement 111 to convey incorrectly labeled bottles, removes any bottles B which have been incorrectly labeled as may have been determined by an inspecting device or an inspecting station, or an inspecting module 128 that may possibly form a part of the labeling arrangement or labeling station 108 having at least one labeling unit, device, or module for first product, each unit having a head.

In FIG. 1A item 112 is a central control arrangement or, expressed differently, a controller with a computer to process algorithms, which controls the operation of the above-referenced system or plant.

The beverage filling machine 105 is preferably of the revolving design, with a rotor 105', which revolves around a vertical machine axis. The rotor 105' is designed to handle the bottles B by the neck. A filling arrangement 114 having at least one filling device, element, apparatus, or valve, comprises an apparatus configured to introduce a predetermined volume of liquid beverage filling material into the interior of bottles B to a predetermined level of liquid beverage filling material. Furthermore, the filling device or apparatus comprises an apparatus configured to terminate the filling of bottles upon liquid beverage filling material reaching the predetermined level in bottles B. In other words, the filling arrangements 114 having at least one filling device, element, apparatus, or valve, are configured and disposed to provide a predetermined flow of liquid beverage filling material from the source thereof, such as, product mixers 123 and 124, into the bottles B.

The toroidal vessel 117 is a component, for example, of the revolving rotor 105'. The toroidal vessel 117 can be connected by means of a rotary coupling or a coupling that permits rotation, and by means of the conduit for first product 121 to the external reservoir or first product mixer 123 to supply the product.

As well as the more typical filling machines having one toroidal vessel, it is possible that in at least one possible embodiment a filling machine could possibly be utilized wherein each filling arrangement 114 having at least one filling device, element, apparatus, or valve is preferably connected by means of two connections to a toroidal vessel 117 which contains a first product, say by means of a first connection, for example, the conduit for first product 121, and to a second toroidal vessel which contains a second product, say by means of the second connection, for example, the conduit for second product 122. In this case, each filling arrangement 114 having at least one filling device, element, apparatus, or valve can also preferably have, at the connections, two individually-controllable fluid or control valves, so that in each bottle B which is delivered at the inlet of the filling machine 105 to a filling position 113, the first product or the second product can be filled by means of an appropriate control of the filling product or fluid valves.

It will be understood that while a two-product assembly or system of a bottling plant is illustrated in FIG. 1A, the disclosure is equally applicable to single-product installations, or other commensurate embodiments.

FIG. 1A further shows a beverage treatment device 200, which beverage treatment device 200 is connected to the first product mixer 123 and the second product mixer 124 to treat the beverage when the beverage is in the mixers 123, 124. FIG. 1A also shows a beverage bottle treatment station 250 disposed substantially between the bottle closing station 106 and the bottle labeling station 108. The beverage bottle treatment station 250 further treats the beverage material in the closed, filled bottles. A transfer line 275 is shown in FIG. 1A, which transfer line 275 transfers and recycles the treatment material between said beverage treatment device and said beverage bottle treatment station.

Figure 1B:
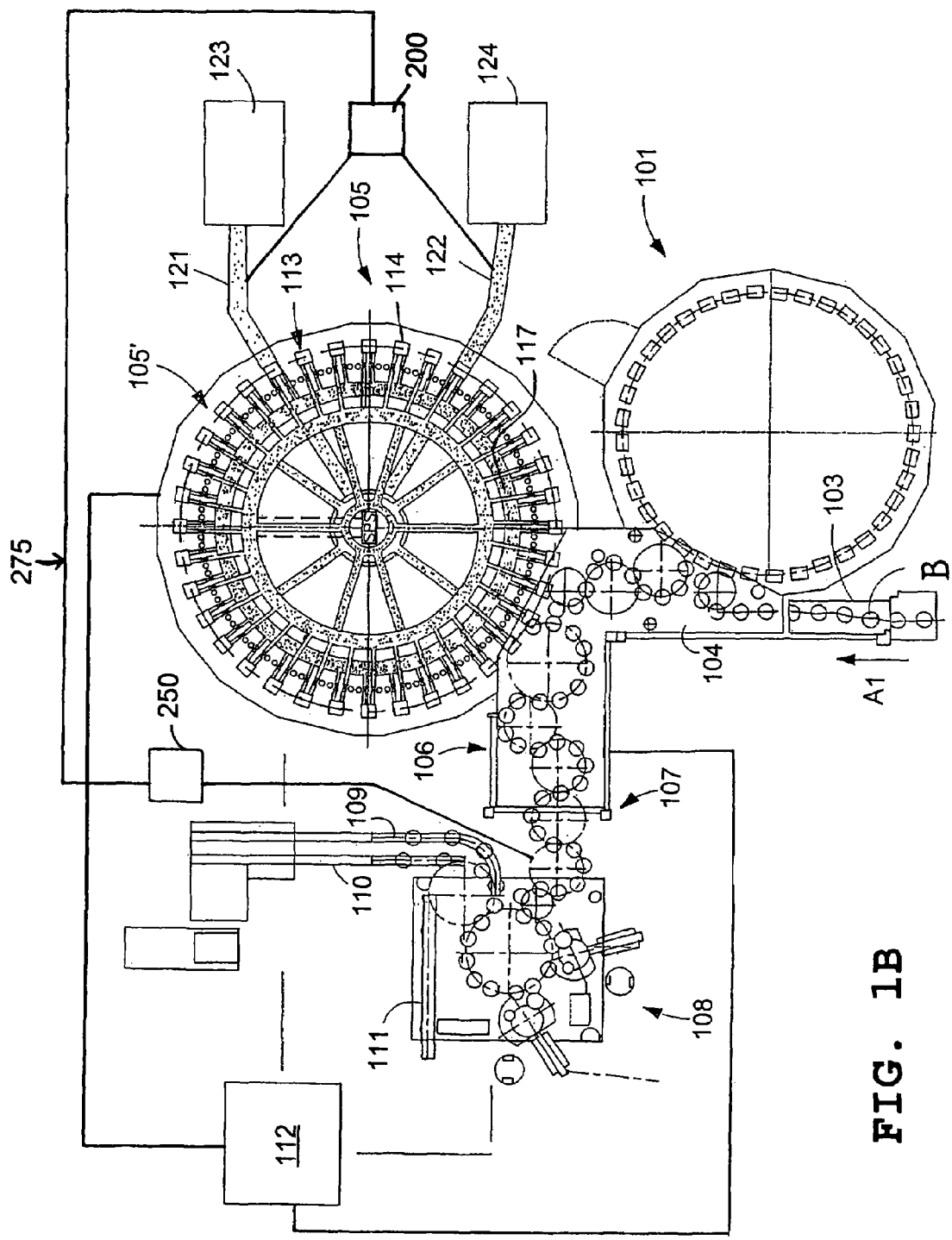
FIG. 1B is similar to FIG. 1A, and shows another possible embodiment of a container filling plant.

FIG. 1B is similar to FIG. 1A, and shows an alternate embodiment where a beverage treatment device 200 is connected to the conduit for first product 121 and the conduit for second product 122 to treat the beverage product when the beverage product is in the conduits 121, 122.

Figure 1C:
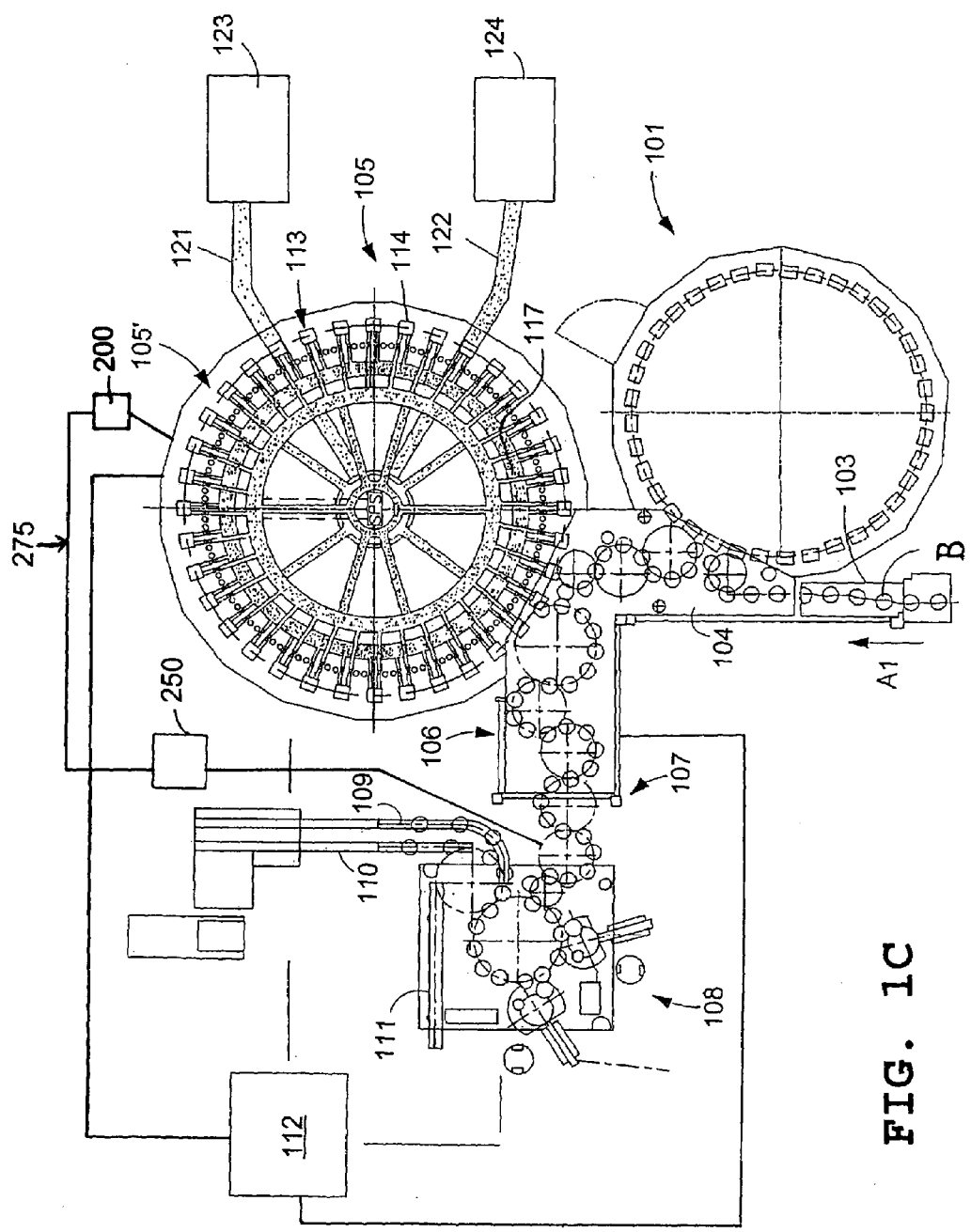
FIG. 1C is similar to FIGS. 1A and 1B, and shows another possible embodiment of a container filling plant.

FIG. 1C is similar to FIGS. 1A and 1B, and shows an alternate embodiment where a beverage treatment device 200 is connected to the beverage filling machine to treat the beverage when it is located in the beverage filling machine.

Figure 1D:
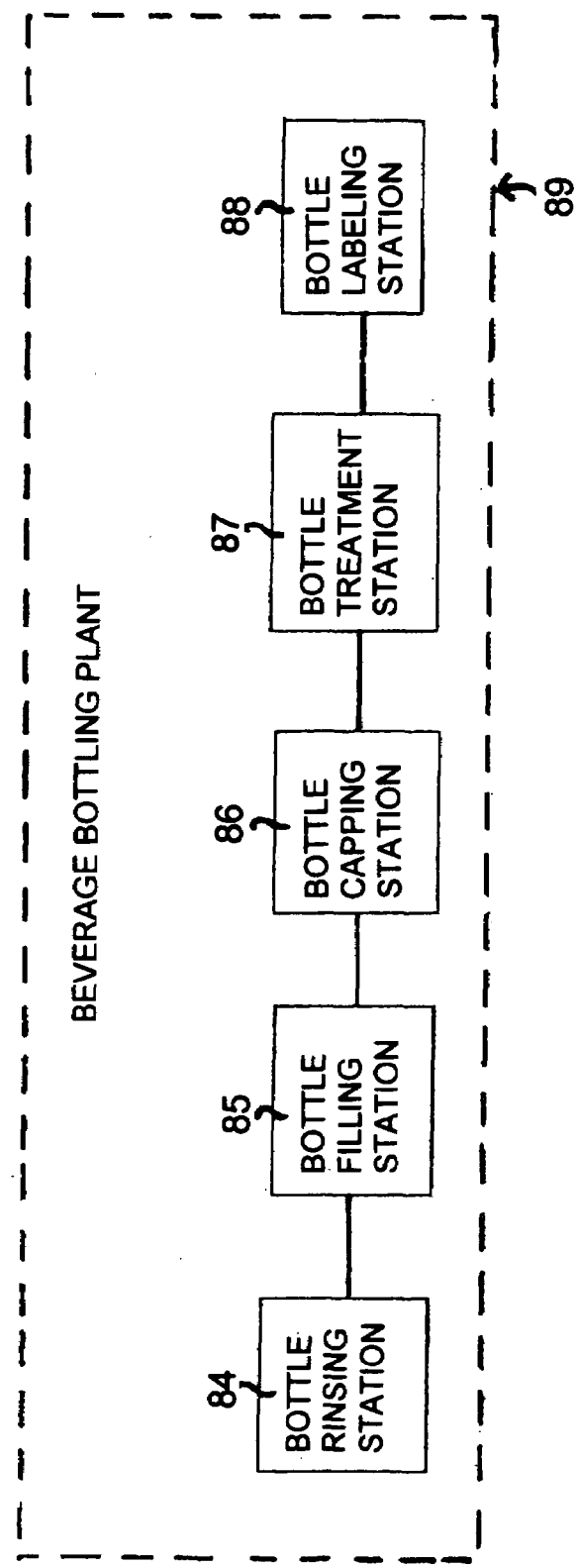
FIG. 1D is a block diagram of a beverage bottling plant and its sections.

FIG. 1D is a block diagram of a beverage bottling plant 89 and the sections 84-88 of this plant 89. Beverage bottles or other containers move through the bottling plant 89 in the following order: beverage bottle rinsing station 84; beverage bottle filling station 85; beverage bottle capping station 86; beverage bottle treatment station 87; and beverage bottle labeling station 88. In one possible embodiment, the beverage bottle treatment station 87 may be a heat treatment station.

Figure 1:
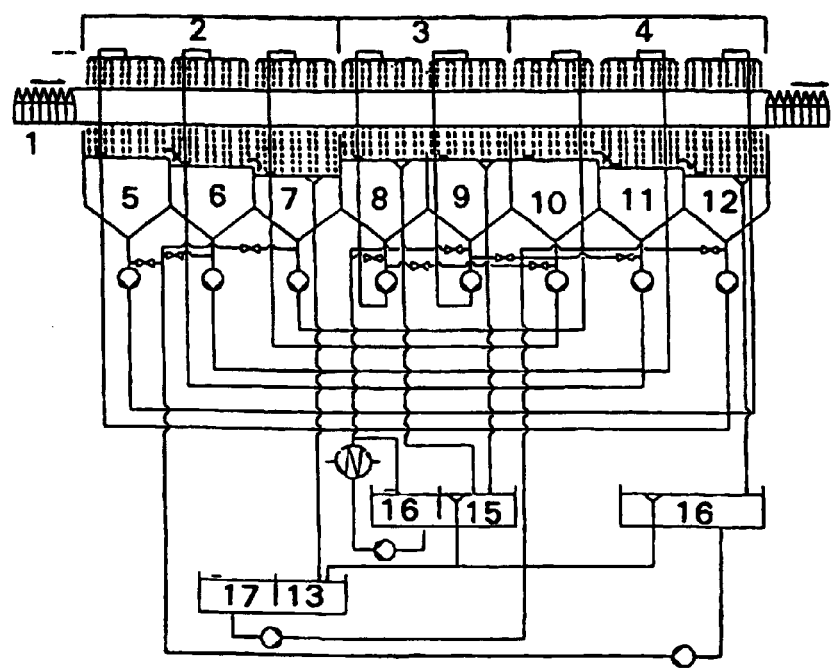
FIG. 1 shows a general treatment plant and the sequences of processes that are carried out in it.

As shown in FIG. 1, the treatment plant comprises a heating section 2 which is in the entry area, seen in the direction of travel of the respective containers 1, whereby the heating section 2 can comprise a plurality of individual zones 5-7, as a result of which the heating phase can be carried out gradually. Downstream of this heating section 2 is a superheating zone 8, and after that there is the actual treatment zone 9. Then begins the area of the cooling section 4 which, like the other sections, can comprise a larger number of individual zones 10-12.

The operating program of a treatment plant of this type is designed primarily so that the treatment process can be carried out under optimal conditions. For example, the first heating zone 5 has a spray temperature of 18° C. The output temperature of the treated products is correspondingly achieved with a spraying temperature of approximately 17° C. The second heating zone 6 has a spraying temperature slightly higher than 24° C., whereby the cooling zone that communicates with it can in turn be at a slightly lower temperature of 23° C. From the example of these two zones, it can be seen that the water from the "cooling" zones 4 is transported to the zone in the "heating" section 2, the desired heating temperature of which is the closest to the desired cooling temperature. To equalize any temperature difference, water from the first reservoir 13, whose higher-temperature water originates from the final station 7 of the heating section 2, is added in small quantities to the water from the cooling segment 4. Downstream of this heating section is the superheating zone 8, the temperature of which is in turn higher than the temperature of the final heating zone 7 and is supplied from a second reservoir 15 which is at a higher temperature than the first reservoir 13. Associated with the second reservoir 14 is a third reservoir 16 to which the excess water from the reservoir 15 is fed. This third reservoir 16 is also kept at a predetermined higher temperature by means of a heating device. The superheating and treatment zones 8, 9 are also sprayed with water from this reservoir 16, whereby the hot water that drains off is collected in the second reservoir 15 and mixed with the hot water from the third reservoir 16.

In the event of a disruption, for example an interruption caused by a backup of bottles in the treatment plant, a control device (not shown in any greater detail) immediately actuates certain valves so that, for example, the lower-temperature water from the first reservoir 13 is fed to the superheating and/or treatment zones 8, 9.

Lower-temperature water can also be supplied to the other section 2, 4, for example from an additional fourth reservoir 14.

Figure 2:
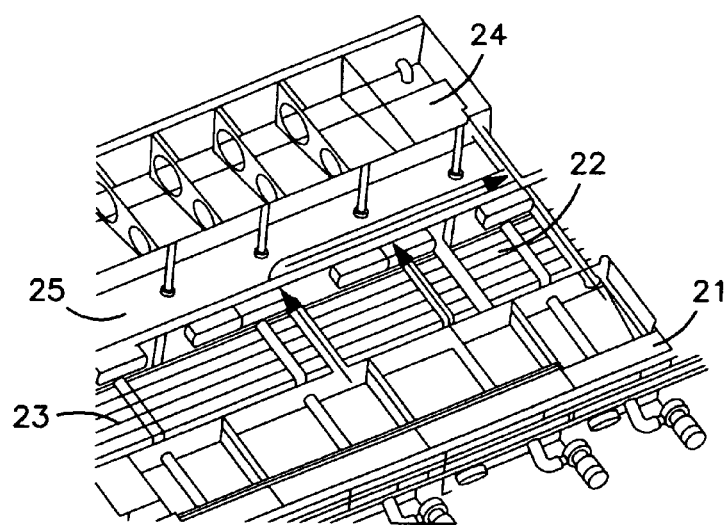
FIGS. 2 to 5 illustrate the corresponding realization of a housing in the form of one exemplary embodiment.

The device itself illustrated in FIGS. 2 to 5 in the form of a treatment housing is a modular housing construction that comprises a plurality of segments, whereby the substructure comprises pre-assembled zone tanks 21 with pipelines, valves and cabling, which are associated laterally with all of the pipelines 22 or with individual segments thereof. Segments 24 of the hot water buffer tanks run at some distance from them. The space between is left open as a crawl space 25 for service operations, as illustrated in FIG. 2.

Figure 3:
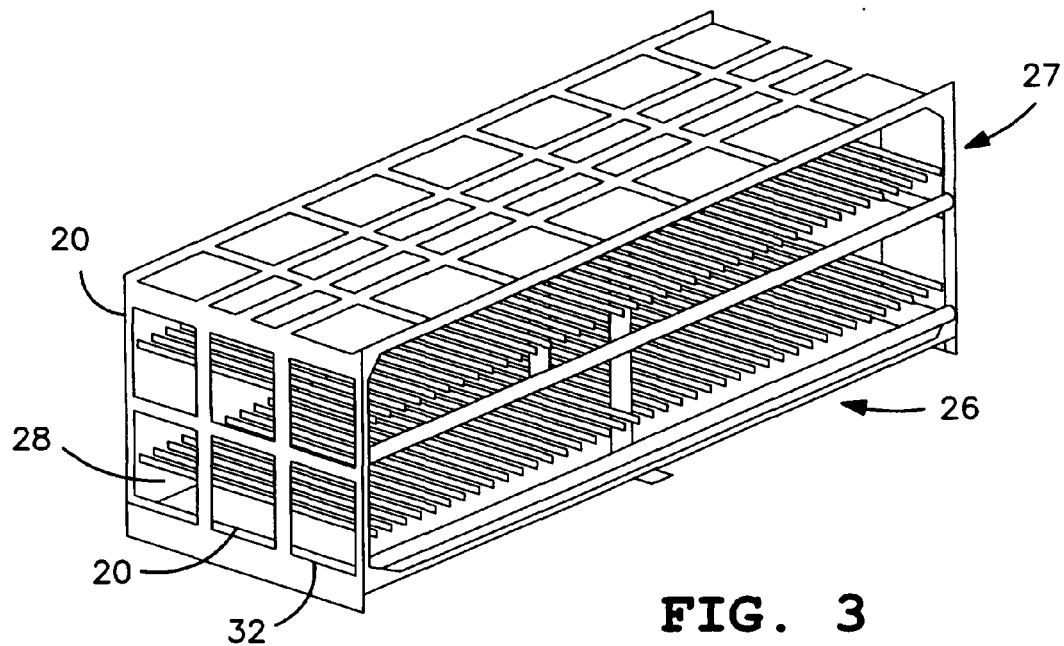
Figure 4:
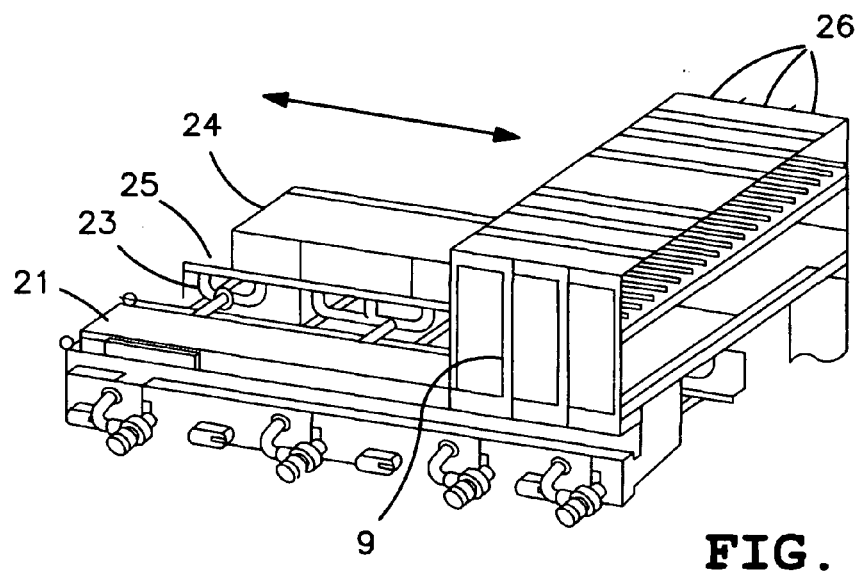

FIG. 3 shows the replaceable and flexible segment 6 of the tunnel housing itself. These individual segments contain the conveyor belt substructure with a return-side belt support as well as the spray distributors and a roof structure, preferably with external reinforcement fins. The side openings 28 can be sealed with side panels 29 that can be attached on the sides. As shown in FIG. 4, the treatment segments 26 run at a right angle to the direction of transport of the treatment device and are placed on the zone tank 21 and the hot water tank 24 which is at some distance from the zone tank 21. The treatment segments 26 are equipped in the base area with slide elements, assembly rollers or convertible casters to simplify local displacement, and can be moved in the horizontal plane as well as positioned in a row next to one another.

Figure 5:
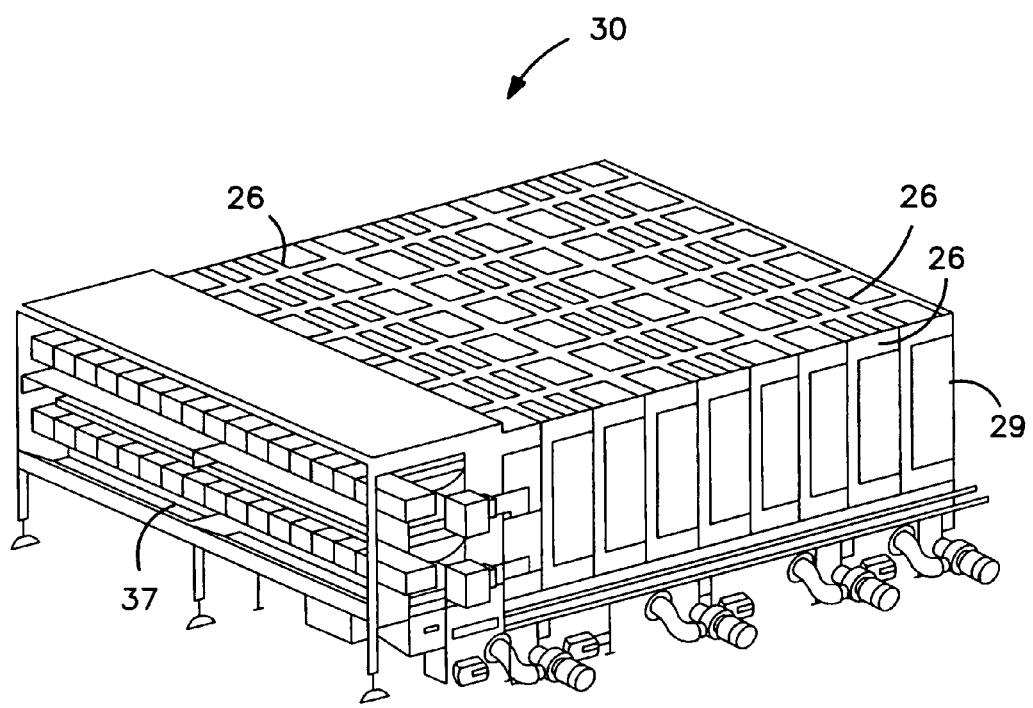

In this manner, as shown in FIG. 5, the tunnel segments 5 form a compact housing structure 30, which by attaching the individual feed segment 31 and the individual discharge segment 31 on the end form a complete treatment plant that can be reduced in size or expanded at any time. The machine width thereby essentially also forms the handling width, whereby the compact housing structure is bordered only by narrow side panels 29. These panels are held without gaskets or seals in the side wall configurations 20 of the segments 26, and are advantageously supported in a bottom frame 32 that conducts water. In place of these treatment segments that are oriented at a right angle to the direction of conveyance of the treatment device, segments can also be used that can be lined up one after the other parallel to the direction of conveyance, whereby the substructures in the form of tanks 21 and 24 are oriented at a right angle to the actual direction of conveyance.

The frame of the segments 26 can be formed from tubes, rectangular tubes or similar components. The fittings such as spray tubes, spray distributors, the conveyor belt substructure, return-side belt support and additional components are preferably integral components of the segment construction and are thus also provided to impart rigidity to the system. The standardized housing segments are realized in the form of installation modules, whereby their dimensions correspond to the conventionally permitted inside dimensions of containers, e.g. of a standard freight container.

The zone tanks can also be equipped with debris screening and removal conveyors and splinter washout systems. In the regenerative zones, there is cascading cold or hot water circulation for the optimal utilization of the energy of the hot and/or cold water. The water is transported by means of graduated weirs, whereby the level in the individual zones is maintained by suitable means such as appropriate sensors and frequency-controlled pumps, for example.

The treatment plant can preferably be assembled and installed as disclosed herein below.

In the beverage industry, especially when bottling highly perishable products, it is customary to pasteurize them. In pasteurizing plants of the prior art, the containers with the products are conveyed in a practically uniform and continuous movement from the entry area to the exit area. During this movement, they are heated until they have absorbed the desired number of pasteurization units, then cooled, whereupon the pasteurizing process is ended. A pasteurizing tunnel provided for the purpose consequently has a heating section, a superheating and pasteurizing section and a subsequent cooling section. The individual sections can have additional sub-zones. The gradual heating and cooling thereby achieved is preferred in particular for the glass bottles used in the beverage industry, to avoid the destruction of the glass bottles by abrupt temperature changes. The transfer of heat to the product contained in the bottles is normally achieved by spraying said containers with water as they are moved along on a conveyor belt which allows the sprayed liquid to pass through from below. Underneath the conveyor belt are catch basins for the sprayed fluid, from which the pumps used for the spraying are fed. Between the heating and cooling sections, heat can be exchanged with the sprayed liquid in the individual zones.

To achieve an optimum graduation of the temperatures in the individual sections, the sections are appropriately subdivided. Generally, the "heating" section has three to four individual zones, the pasteurizing section has two or three zones, and an additional superheating zone can also be provided upstream of the pasteurizing zone. The subsequent "cooling" section in turn has three to four individual zones in which the containers are cooled to the desired exit temperature by decreasing the temperature of the sprayed liquid in steps.

The spray temperatures that are set at any given time are adjusted so that they are appropriate to the product, the length of the zones and the speed of the conveyor belt to ensure that the product in the bottles achieves the specified degree of pasteurization.

For the spraying of the containers, in the pasteurizer housing, oriented at right angles to the direction of transport, there are a plurality of spray tubes with spray nozzles or spray openings next to one another and at a distance from one another, and a lateral fluid feed. Spray tubes of this type are known from DE 297 166 44, for example.

On the basis of a pasteurizing plant of the type described above, the object of the present application is to reduce the time, effort and expense required for the manufacture, assembly and start-up of these plants and their pasteurizing housings, and to create standardized housing modules, preferably for almost all types of realizations.

The present application teaches that the pasteurizer housing is formed in a modular configuration from any desired number of flexible, exchangeable interchangeable segments, whereby these segments are oriented at a right angle to or parallel to the direction of conveyance of the pasteurizer, and can be positioned and lined up next to one another on zone tanks or hot water tanks that are oriented parallel to or along this conveyor device.

With this configuration and the features disclosed in the other claims, as well as in this description, the result is simple housing base modules that have a high percentage of identical parts and that permit series production of many components. In addition, there is a more flexible zone structure for an optimal machine design, whereby the essentially standardized housing modules are suitable for almost all types of realizations of heat treatment machines for containers such as pasteurizers, coolers, heaters etc.

In this case, the pasteurizing plant comprises a heating section 2 which is in the entry area, seen in the direction of travel of the respective containers 1, whereby the heating section 2 can comprise a plurality of individual zones 5-7, as a result of which the heating phase can be carried out gradually. Downstream of this heating section 2 is a superheating zone 8, and after that there is the actual pasteurizing zone 9. Then begins the area of the cooling section 4 which, like the other sections, can comprise a larger number of individual zones 10-12.

The operating program of a pasteurizing plant of this type is designed primarily so that the pasteurizing process can be carried out under optimal conditions. For example, the first heating zone 5 has a spray temperature of 18° C. The output temperature of the pasteurized products is correspondingly achieved with a spraying temperature of approximately 17° C. The second heating zone 6 has a spraying temperature slightly higher than 24° C., whereby the cooling zone that communicates with it can in turn be at a slightly lower temperature of 23° C. From the example of these two zones, it can be seen that the water from the "cooling" zones 4 is transported to the zone in the "heating" section 2, the desired heating temperature of which is the closest to the desired cooling temperature. To equalize any temperature difference, water from the first reservoir 13, whose higher-temperature water originates from the final station 7 of the heating section 2, is added in small quantities to the water from the cooling segment 4. Downstream of this heating section is the superheating zone 8, the temperature of which is in turn higher than the temperature of the final heating zone 7 and is supplied from a second reservoir 15 which is at a higher temperature than the first reservoir 13. Associated with the second reservoir 14 is a third reservoir 16 to which the excess water from the reservoir 15 is fed. This third reservoir 16 is also kept at a predetermined higher temperature by means of a heating device. The superheating and pasteurizing zones 8, 9 are also sprayed with water from this reservoir 16, whereby the hot water that drains off is collected in the second reservoir 15 and mixed with the hot water from the third reservoir 16.

In the event of a disruption, for example an interruption caused by a backup of bottles in the pasteurizing plant, a control device (not shown in any greater detail) immediately actuates certain valves so that, for example, the lower-temperature water from the first reservoir 13 is fed to the superheating and/or pasteurizing zones 8, 9.

Lower-temperature water can also be supplied to the other section 2, 4, for example from an additional fourth reservoir 14.

The device itself illustrated in FIGS. 2 to 5 in the form of a pasteurizing housing is a modular housing construction that comprises a plurality of segments, whereby the substructure comprises pre-assembled zone tanks 21 with pipelines, valves and cabling, which are associated laterally with all of the pipelines 22 or with individual segments thereof. Segments 24 of the hot water buffer tanks run at some distance from them. The space between is left open as a crawl space 25 for service operations, as illustrated in FIG. 2.

FIG. 3 shows the replaceable and flexible segment 6 of the tunnel housing itself. These individual segments contain the conveyor belt substructure with a return-side belt support as well as the spray distributors and a roof structure, preferably with external reinforcement fins. The side openings 28 can be sealed with side panels 29 that can be attached on the sides. As shown in FIG. 4, the pasteurizer segments 26 run at a right angle to the direction of transport of the pasteurizer and are placed on the zone tank 21 and the hot water tank 24 which is at some distance from the zone tank 21. The pasteurizer segments 26 are equipped in the base area with slide elements, assembly rollers or convertible casters to simplify local displacement, and can be moved in the horizontal plane as well as positioned in a row next to one another.

In this manner, as shown in FIG. 5, the tunnel segments 5 form a compact housing structure 30, which by attaching the individual feed segment 31 and the individual discharge segment 31 on the end form a complete pasteurization plant that can be reduced in size or expanded at any time. The machine width thereby essentially also forms the handling width, whereby the compact housing structure is bordered only by narrow side panels 29. These panels are held without gaskets or seals in the side wall configurations 20 of the segments 26, and are advantageously supported in a bottom frame 32 that conducts water. In place of these pasteurizer segments that are oriented at a right angle to the direction of conveyance of the pasteurizer, segments can also be used that can be lined up one after the other parallel to the direction of conveyance, whereby the substructures in the form of tanks 21 and 24 are oriented at a right angle to the actual direction of conveyance.

The frame of the segments 26 can be formed from tubes, rectangular tubes or similar components. The fittings such as spray tubes, spray distributors, the conveyor belt substructure, return-side belt support and additional components are preferably integral components of the segment construction and are thus also provided to impart rigidity to the system. The standardized housing segments are realized in the form of installation modules, whereby their dimensions correspond to the conventionally permitted inside dimensions of containers, e.g. of a standard freight container.

The zone tanks can also be equipped with debris screening and removal conveyors and splinter washout systems. In the regenerative zones, there is cascading cold or hot water circulation for the optimal utilization of the energy of the hot and/or cold water. The water is transported by means of graduated weirs, whereby the level in the individual zones is maintained by suitable means such as appropriate sensors and frequency-controlled pumps, for example.

The pasteurizing plant can preferably be assembled and installed as disclosed herein.

A further feature or aspect of an embodiment is believed at the time of the filing of this patent application to possibly reside broadly in a pasteurizing plant for the pasteurizing of products in containers that are handled in a stream of containers by sequential sections at least for heating, pasteurizing and cooling by means of liquid that is poured over them, and with a pasteurizing housing and transport, spray and other devices, pans, pumps etc., characterized by the fact that the tunnel housing is formed in a modular configuration from any desired number of flexible, exchangeable segments, whereby said segments extend at a right angle or parallel to the direction of conveyance of the pasteurizer, and can be lined up one behind another on zone tanks and/or hot water tanks that are oriented parallel to or along said direction of conveyance.

Another feature or aspect of an embodiment is believed at the time of the filing of this patent application to possibly reside broadly in a pasteurizing plant, characterized by the fact that next to the external zone tanks lined up in a row, and underneath the segments supported on said tanks, there is at least one additional pipeline element that is pre-assembled in segments and a space is provided for service on the lower areas.

Yet another feature or aspect of an embodiment is believed at the time of the filing of this patent application to possibly reside broadly in a pasteurizing plant, characterized by the fact that zone tanks in a pre-assembled configuration are equipped with the necessary pipelines, valves, motors, cabling etc.

Still another feature or aspect of an embodiment is believed at the time of the filing of this patent application to possibly reside broadly in a pasteurizing plant, characterized by the fact that the actual feed segment and the actual discharge segment can be attached on the ends to the segments that form a compact housing structure in a modular arrangement.

A further feature or aspect of an embodiment is believed at the time of the filing of this patent application to possibly reside broadly in a pasteurizing plant, characterized by the fact that the machine width essentially also forms the handling width, and the compact housing structure is bordered only by narrow side panels.

Another feature or aspect of an embodiment is believed at the time of the filing of this patent application to possibly reside broadly in a pasteurizing plant, characterized by the fact that the side panels form a watertight housing side wall without gaskets or seals and are held at least in the lower area in a frame that conducts and drains water.

Still another feature or aspect of an embodiment is believed at the time of the filing of this patent application to possibly reside broadly in a pasteurizing plant, characterized by the fact that the segments have at least one conveyor belt substructure, one return-side belt support, distributors for the spray water and a roof structure.

Yet another feature or aspect of an embodiment is believed at the time of the filing of this patent application to possibly reside broadly in a pasteurizing plant, characterized by the fact that the segments have means to simplify the assembly of the segments.

A further feature or aspect of an embodiment is believed at the time of the filing of this patent application to possibly reside broadly in a pasteurizing plant, characterized by the fact that said means are assembly rollers.

Another feature or aspect of an embodiment is believed at the time of the filing of this patent application to possibly reside broadly in a pasteurizing plant, characterized by the fact that said means are casters, the direction of action of which can be adjusted.

Still another feature or aspect of an embodiment is believed at the time of the filing of this patent application to possibly reside broadly in a pasteurizing plant, characterized by the fact that the segments can be rolled and/or slid into position in a guided manner on the hot water and/or zone tanks on which they are supported.

Yet another feature or aspect of an embodiment is believed at the time of the filing of this patent application to possibly reside broadly in a pasteurizing plant, characterized by the fact that the frame of the segments is realized from rectangular tubes.

A further feature or aspect of an embodiment is believed at the time of the filing of this patent application to possibly reside broadly in a pasteurizing plant, characterized by the fact that the fixtures such as spray tubes etc. are an integral component of the segment construction and provide the system with rigidity.

Another feature or aspect of an embodiment is believed at the time of the filing of this patent application to possibly reside broadly in a pasteurizing plant, characterized by the fact that the segments positioned on the zone and/or hot water tanks can be displaced and/or positioned in the horizontal plane.

Yet another feature or aspect of an embodiment is believed at the time of the filing of this patent application to possibly reside broadly in a pasteurizing plant, characterized by the fact that the standardized housing segments are realized in the form of assembly modules, the dimensions of which correspond to the allowable inside dimensions of standard freight containers.

Still another feature or aspect of an embodiment is believed at the time of the filing of this patent application to possibly reside broadly in a method for the assembly of a pasteurizing housing of a pasteurizing plant, characterized by the fact that modularized function blocks in the form of segments are put together on the basis of a specified plan in a coordinated construction process, whereby first the load-bearing floor components are oriented as the actual substructure in the form of tanks and are set to the required width with a space in between, and the pipeline segments provided in the space near the floor are installed, whereupon the segments are positioned in rows on the tanks and the terminal pieces are attached in the form of feed and discharge housings, the conveyor elements are attached and the lateral panels are incorporated, and the final assembly with startup is carried out.

Another feature or aspect of an embodiment is believed at the time of the filing of this patent application to possibly reside broadly in a beverage bottling plant for filling bottles with a liquid beverage filling material, said beverage bottling plant comprising: a bottle cleaning machine being configured and disposed to clean empty bottles; a feed arrangement to supply empty bottles to said bottle cleaning machine; a beverage filling machine being configured and disposed to fill empty bottles with liquid beverage material; said beverage filling machine comprising a plurality of beverage filling devices for filling bottles with liquid beverage material; at least one storage unit being configured and disposed to store a supply of liquid beverage material; at least one supply line being configured and disposed to connect said at least one storage unit to said beverage filling machine to supply liquid beverage material to said beverage filling machine; a beverage treatment device being configured and disposed to treat with a treatment material said liquid beverage filling material in one of: said at least one storage unit, said at least one supply line, and said beverage filling machine; a first conveyer arrangement being configured and disposed to move empty bottles from said bottle cleaning machine into said beverage filling machine; said first conveyer arrangement comprising a star wheel structure; a bottle closing machine being configured and disposed to close tops of filled beverage bottles; a second conveyer arrangement being configured and disposed to move filled beverage bottles from said beverage filling machine into said bottle closing machine; said second conveyer arrangement comprising a star wheel structure; a beverage bottle treatment station being configured and disposed to further treat liquid beverage material in filled, closed beverage bottles; said treatment material is recycled between and used in both said beverage treatment device and said beverage bottle treatment station; a third conveyer arrangement being configured and disposed to move filled, closed beverage bottles from said bottle closing machine into said beverage bottle treatment station; said third conveyer arrangement comprising a star wheel structure; a beverage bottle labeling station being configured and disposed to label filled, closed beverage bottles; a fourth conveyor arrangement being configured and disposed to move filled, closed beverage bottles from said beverage bottle treatment station into said beverage bottle labeling station; said fourth conveyer arrangement comprising a star wheel structure; said beverage bottle treatment station comprising: a tunnel housing formed in a modular configuration from any desired number of flexible, exchangeable segments; said segments extending at a right angle or parallel to the direction of conveyance of the treatment station; and said segments can be lined up one behind another on zone tanks and/or hot water tanks that are oriented parallel to or along said direction of conveyance.

The components disclosed in the various publications, disclosed or incorporated by reference herein, may possibly be used in possible embodiments, as well as equivalents thereof.

Some examples of beverage bottling systems which may possibly be utilized or adapted for use in at least one possible embodiment may possibly be found in the following U.S. Patents, and are hereby incorporated by reference as if set forth in their entirety herein: U.S. Pat. No. 6,494,238, entitled "Plant for filling beverage into beverage bottles and other beverage containers having apparatus for replacing remaining air volume in filled beverage bottles or other beverage containers;" U.S. Pat. No. 6,474,368, entitled "Beverage container filling machine, and method for filling containers with a liquid filling material in a beverage container filling machine;" U.S. Pat. No. 6,470,922, entitled "Bottling plant for bottling carbonated beverages;" U.S. Pat. No. 6,463,964, entitled "Method of operating a machine for filling bottles, cans or the like beverage containers with a beverage, and a beverage container filling machine;" U.S. Pat. No. 6,374,575, entitled "Bottling plant and method of operating a bottling plant;" U.S. Pat. No. 6,365,054, entitled "Plant for filling containers and a method for operating a plant for filling containers," U.S. Pat. No. 6,192,946, entitled "Bottling system;"

U.S. Pat. No. 6,189,578, entitled "Filling system and filling element;" U.S. Pat. No. 6,058,985, entitled "Bottling machine with a set-up table and a set-up table for a bottling machine and a set-up table for a bottle handling machine;" U.S. Pat. No. 5,713,403, entitled "Method and system for filling containers with a liquid filling product, and filling machine and labeling device for use with this method or system," U.S. Pat. No. 5,634,500, entitled "Method for bottling a liquid in bottles or similar containers;" and U.S. Pat. No. 5,413,153, entitled "Container filling machine for filling open-top containers, and a filler valve therefor."

The purpose of the statements about the technical field is generally to enable the Patent and Trademark Office and the public to determine quickly, from a cursory inspection, the nature of this patent application. The description of the technical field is believed, at the time of the filing of this patent application, to adequately describe the technical field of this patent application. However, the description of the technical field may not be completely applicable to the claims as originally filed in this patent application, as amended during prosecution of this patent application, and as ultimately allowed in any patent issuing from this patent application. Therefore, any statements made relating to the technical field are not intended to limit the claims in any manner and should not be interpreted as limiting the claims in any manner.

Some examples of modular building structures which may possibly be utilized or adapted for use in at least one possible embodiment may possibly be found in the following U.S. Patents: U.S. Pat. No. 5,906,075, entitled "Modular building structure;" U.S. Pat. No. 6,256,960, entitled "Modular building construction and components thereof;" U.S. Pat. No. 5,644,871, entitled "Modular building system;" U.S. Pat. No. 5,371,988, entitled "Modular building system and frame members;" U.S. Pat. No. 5,103,604, entitled "Modular building systems;" U.S. Pat. No. 6,089,393, entitled "Modular structure for constituting an enclosure."

The appended drawings in their entirety, including all dimensions, proportions and/or shapes in at least one embodiment of the invention, are accurate and are hereby included by reference into this specification.

Some examples of heat exchangers which may possibly be utilized or adapted for use in at least one possible embodiment may possibly be found in the following U.S. Patents: U.S. Pat. No. 4,665,975, entitled "Plate type heat exchanger;" U.S. Pat. No. 6,810,948, entitled "Heat exchanger;" U.S. Pat. No. 6,799,428, entitled "Heat exchanger;" U.S. Pat. No. 6,394,179, entitled "Plate heat exchanger;" U.S. Pat. No. 6,125,649, entitled "Heat exchanger unit with conductive discs;" U.S. Pat. No. 5,579,650, entitled "Heat exchanger;" and U.S. Pat. No. 4,313,491, entitled "Coiled heat exchanger."

The background information is believed, at the time of the filing of this patent application, to adequately provide background information for this patent application. However, the background information may not be completely applicable to the claims as originally filed in this patent application, as amended during prosecution of this patent application, and as ultimately allowed in any patent issuing from this patent application. Therefore, any statements made relating to the background information are not intended to limit the claims in any manner and should not be interpreted as limiting the claims in any manner.

All, or substantially all, of the components and methods of the various embodiments may be used with at least one embodiment or all of the embodiments, if more than one embodiment is described herein.

Some examples of temperature sensors or sensor systems that may be used or adapted for use in at least one possible embodiment of the present invention may be found in the following U.S. patents: U.S. Pat. No. 5,960,857, issued to inventors Oswalt et al. on Oct. 5, 1999; U.S. Pat. No. 5,942,980, issued to inventors Hoben et al. on Aug. 24, 1999; U.S. Pat. No. 5,881,952, issued to inventor MacIntyre on Mar. 16, 1999; U.S. Pat. No. 5,862,669, issued to inventors Davis et al. on Jan. 26, 1999; U.S. Pat. No. 5,459,890, issued to inventor Jarocki on Oct. 24, 1995; U.S. Pat. No. 5,367,602, issued to inventor Stewart on Nov. 22, 1994; U.S. Pat. No. 5,319,973, issued to inventors Crayton et al. on Jun. 14, 1994; U.S. Pat. No. 5,226,320, issued to inventors Dages et al. on Jul. 13, 1993; U.S. Pat. No. 5,078,123, issued to inventors Nagashima et al. on Jan. 7, 1992; and U.S. Pat. No. 5,068,030, issued to inventor Chen on Nov. 26, 1991.

The purpose of the statements about the object or objects is generally to enable the Patent and Trademark Office and the public to determine quickly, from a cursory inspection, the nature of this patent application. The description of the object or objects is believed, at the time of the filing of this patent application, to adequately describe the object or objects of this patent application. However, the description of the object or objects may not be completely applicable to the claims as originally filed in this patent application, as amended during prosecution of this patent application, and as ultimately allowed in any patent issuing from this patent application. Therefore, any statements made relating to the object or objects are not intended to limit the claims in any manner and should not be interpreted as limiting the claims in any manner.

Some examples of position sensors or position sensor systems that may be used or adapted for use in at least one possible embodiment of the present invention may be found in the following U.S. patents: U.S. Pat. No. 5,794,355, issued to inventor Nickum on Aug. 18, 1998; U.S. Pat. No. 5,520,290, issued to inventors Kumar et al. on May 28, 1996; U.S. Pat. No. 5,074,053, issued to inventor West on Dec. 24, 1991; and U.S. Pat. No. 4,087,012, issued to inventor Fogg on May 2, 1978.

All of the patents, patent applications and publications recited herein, and in the Declaration attached hereto, are hereby incorporated by reference as if set forth in their entirety herein.

The summary is believed, at the time of the filing of this patent application, to adequately summarize this patent application. However, portions or all of the information contained in the summary may not be completely applicable to the claims as originally filed in this patent application, as amended during prosecution of this patent application, and as ultimately allowed in any patent issuing from this patent application. Therefore, any statements made relating to the summary are not intended to limit the claims in any manner and should not be interpreted as limiting the claims in any manner.

Some examples of heaters or heat exchangers, cooling systems, valves, pumps, or tanks that may be used or adapted for use in at least one possible embodiment of the present invention may be found in the following U.S. patents: U.S. Pat. No. 5,881,952, issued to inventor Macintyre on Mar. 16, 1999; U.S. Pat. No. 5,862,669, issued to inventors Davis et al. on Jan. 26, 1999; U.S. Pat. No. 5,459,890, issued to inventor Jarocki on Oct. 24, 1995; U.S. Pat. No. 5,367,602, issued to inventor Stewart on Nov. 22, 1994; U.S. Pat. No. 5,319,973, issued to inventors Crayton et al. on Jun. 14, 1994; U.S. Pat. No. 5,226,320, issued to inventors Dages et al. on Jul. 13, 1993; U.S. Pat. No. 5,078,123, issued to inventors Nagashima et al. on Jan. 7, 1992; and U.S. Pat. No. 5,068,030, issued to inventor Chen on Nov. 26, 1991.

It will be understood that the examples of patents, published patent applications, and other documents which are included in this application and which are referred to in paragraphs which state "Some examples of . . . which may possibly be used in at least one possible embodiment of the present application . . . " may possibly not be used or useable in any one or more embodiments of the application.

The sentence immediately above relates to patents, published patent applications and other documents either incorporated by reference or not incorporated by reference.

The corresponding foreign and international patent publication applications, namely, Federal Republic of Germany Patent Application No. 103 52 886.5, filed on Nov. 10, 2003, having inventor Ulrich WIEDEMANN, and DE-OS 103 52 886.5 and DE-PS 103 52 886.5, as well as their published equivalents, and other equivalents or corresponding applications, if any, in corresponding cases in the Federal Republic of Germany and elsewhere, and the references and documents cited in any of the documents cited herein, such as the patents, patent applications and publications, are hereby incorporated by reference as if set forth in their entirety herein.

All of the references and documents, cited in any of the documents cited herein, are hereby incorporated by reference as if set forth in their entirety herein. All of the documents cited herein, referred to in the immediately preceding sentence, include all of the patents, patent applications and publications cited anywhere in the present application.

The description of the embodiment or embodiments is believed, at the time of the filing of this patent application, to adequately describe the embodiment or embodiments of this patent application. However, portions of the description of the embodiment or embodiments may not be completely applicable to the claims as originally filed in this patent application, as amended during prosecution of this patent application, and as ultimately allowed in any patent issuing from this patent application. Therefore, any statements made relating to the embodiment or embodiments are not intended to limit the claims in any manner and should not be interpreted as limiting the claims in any manner.

The details in the patents, patent applications and publications may be considered to be incorporable, at applicant's option, into the claims during prosecution as further limitations in the claims to patentably distinguish any amended claims from any applied prior art.

The purpose of the title of this patent application is generally to enable the Patent and Trademark Office and the public to determine quickly, from a cursory inspection, the nature of this patent application. The title is believed, at the time of the filing of this patent application, to adequately reflect the general nature of this patent application. However, the title may not be completely applicable to the technical field, the object or objects, the summary, the description of the embodiment or embodiments, and the claims as originally filed in this patent application, as amended during prosecution of this patent application, and as ultimately allowed in any patent issuing from this patent application. Therefore, the title is not intended to limit the claims in any manner and should not be interpreted as limiting the claims in any manner.

The abstract of the disclosure is submitted herewith as required by 37 C.F.R. §1.72(b). As stated in 37 C.F.R. §1.72 (b):

A brief abstract of the technical disclosure in the specification must commence on a separate sheet, preferably following the claims, under the heading "Abstract of the Disclosure." The purpose of the abstract is to enable the Patent and Trademark Office and the public generally to determine quickly from a cursory inspection the nature and gist of the technical disclosure. The abstract shall not be used for interpreting the scope of the claims. Therefore, any statements made relating to the abstract are not intended to limit the claims in any manner and should not be interpreted as limiting the claims in any manner.

The embodiments of the invention described herein above in the context of the preferred embodiments are not to be taken as limiting the embodiments of the invention to all of the provided details thereof, since modifications and variations thereof may be made without departing from the spirit and scope of the embodiments of the invention.

What is claimed is:

1. A pasteurization station for the pasteurizing of products in containers that are handled in a stream of containers by sequential sections at least for heating, pasteurizing, and cooling the products in containers by means of liquid that is poured over them, and comprising a tunnel housing, transport structure, sprayers, pans, and pumps, wherein the tunnel housing is formed in a modular configuration from any desired number of flexible, exchangeable segments, whereby said segments extend at a right angle or parallel to a direction of conveyance of containers in the tunnel housing, and can be lined up one behind another and supported on at least one of: zone tanks and hot water tanks that are oriented parallel to or along said direction of conveyance, and there is at least one pipeline element that is pre-assembled in segments and disposed underneath the tunnel housing segments, said at least one pipeline element being configured and disposed to recycle poured liquid for further use in heating, pasteurizing, and cooling of the products in containers, and wherein:

next to the external zone tanks lined up in a row, and underneath the segments supported on said tanks, a space is provided for service on the lower areas;

the zone tanks in a pre-assembled configuration are equipped with at least pipelines, valves, motors, and cabling;

a feed segment and a discharge segment can be attached on the ends to the segments that form a compact housing structure in a modular arrangement;

the compact housing structure is bordered only by narrow side panels, and the side panels form a watertight housing side wall without gaskets or seals and are held at least in the lower area in a frame that conducts and drains water, and the segments have at least one conveyor belt substructure, one return-side belt support, distributors for the spray water and a roof structure;

the segments have means to simplify the assembly and installation of the segments, said means comprises one of: assembly rollers and casters, the direction of action of which casters can be adjusted, and wherein the segments can be rolled and/or slid into position in a guided manner on the hot water and/or zone tanks on which they are supported, and the frame of the segments is realized from rectangular tubes; and spray tubes are an integral component of the segment construction and provide the system with rigidity, and the segments positioned on the zone and/or hot water tanks can be displaced and/or positioned in the horizontal plane, and the standardized housing segments are realized in the form of assembly modules, the dimensions of which correspond to the allowable inside dimensions of standard freight containers.

2. A pasteurizing station for pasteurizing a product in containers, said pasteurizing station comprising:
- a pasteurizing tunnel through which containers are to be conveyed;
- said pasteurizing tunnel comprising a housing, a conveyor, and a plurality of dispensers configured and disposed to dispense liquid to modify the temperature of the product in the containers being conveyed through said pasteurizing tunnel;
- a plurality of tanks being disposed along the length of and underneath said pasteurizing tunnel;
- a piping arrangement;
- said plurality of tanks being configured and disposed to receive dispensed liquid used to modify the temperature of the product in the containers and to convey the used, dispensed liquid to said piping arrangement;
- said piping arrangement being configured and disposed to recycle dispensed liquid back to said dispensers in said pasteurizing tunnel for further use in modifying the temperature of the product in the containers; and
- said pasteurizing tunnel further comprising:
  - a first, heating, section being configured to heat the product in the containers to a first temperature;
  - a second, pasteurizing, section being configured to further heat the product in the containers to a second temperature being higher than said first temperature and being sufficient to pasteurize the product in the containers;
  - a third, cooling, section being configured to cool the product in the containers to a third temperature lower than said second temperature;
  - each of said sections being formed by at least one modular and interchangeable segment, wherein each of said segments is interchangeable with at least one other of said segments;
  - each of said segments having a height, length, and width, wherein the length is greater than either of said height or width;
  - each of said segments being disposed with its length transverse to a direction of conveyance of the containers through said pasteurizing tunnel, and being supported on said plurality of tanks;
  - each of said segments comprising a portion of said housing, said conveyor, and said dispensers of said pasteurizing tunnel; and
  - each of said segments being disposed immediately adjacent another segment in alignment to form said pasteurizing tunnel.

3. The pasteurization station according to claim 2, wherein:
- said plurality of tanks and the bottom of said segments supported on said tanks define a space underneath said segments configured to permit access for service work to be performed by a worker; and
- at least a portion of said piping is pre-assembled in segments and disposed in said space.

4. The pasteurization station according to claim 3, wherein:
- said dispensers comprise sprayers;
- each of said segments comprises spray tubes connected to said sprayers to supply liquid to said sprayers; and
- said spray tubes are an integral component of each of said segments and provide each of said segments with rigidity.

5. The pasteurization station according to claim 4, wherein the length, height, and width of each of said modular segments correspond to the inside length, height, and width of a standard freight container.

6. The pasteurization station according to claim 5, wherein:
- each of said segments comprises narrow side panels and a roof structure which together form a portion of said housing of said pasteurizing tunnel; and
- said side panels form a watertight housing side wall without gaskets or seals and are held at least in the lower area in a frame that conducts and drains water.

7. The pasteurization station according to claim 6, wherein:
- each of said segments comprises one of: assembly rollers and casters to permit said segments to be rolled or slid into position in a guided manner on said tanks on which they are supported to simplify the assembly and installation of said segments;
- the direction of action of said casters is adjustable; and
- the frame of each of said segments comprises rectangular tubes.

8. The pasteurization station according to claim 7, wherein:
- each of said plurality of tanks comprises a pre-assembled module comprising pipelines, valves, motors, cabling, and other necessary devices;
- said pasteurizing tunnel comprises a container infeed segment attached to the first segment of said first, heating, section; and
- said pasteurizing tunnel comprises a container discharge segment attached to the last segment of said third, cooling, section.

* * * * *